United States Patent [19]
Watkin et al.

[11] Patent Number: 5,348,159
[45] Date of Patent: Sep. 20, 1994

[54] ENHANCEMENT OF POLYCYANOACRYLATE-DEVELOPED FINGERPRINTS

[75] Inventors: John E. Watkin; Della A. Wilkinson, both of Ottawa, Canada

[73] Assignee: Her Majesty the Queen in Right of Canada as represented by the Solicitor General of Canada, Ottawa, Canada

[21] Appl. No.: 905,325

[22] Filed: Jun. 29, 1992

[51] Int. Cl.$^5$ .................. B65D 69/00; B65D 71/00
[52] U.S. Cl. .................. 206/568; 424/2; 427/1; 427/558
[58] Field of Search .......... 206/568; 427/1, 558; 118/31.5; 424/617, 2

[56] References Cited

U.S. PATENT DOCUMENTS 4,806,380  2/1989  Sato et al. .................. 427/1
5,194,289  3/1993  Butland .................. 427/1

OTHER PUBLICATIONS

Adcock, J. M., "The Development of Latent Fingerprints on Human Skin: The Iodine-Silver Transfer Method", Jan. 6, 1977.

Menzel, E. R. et al, "Fluorescent Metal-Ruhemann's Purple Coordination Compounds: Applications to Latent Fingerprint Detection", Feb. 3, 1989.

Allman, D. S. et al, "Detection of Fingerprints on Skin", Dec. 1991.

*Primary Examiner*—Michael Lusignan
*Attorney, Agent, or Firm*—J. Wayne Anderson

[57] ABSTRACT

The invention disclosed relates to a composition and method for enhancing the contrast of polycyanoacrylate-developed fingerprints and the like. The composition includes a metal chelate of the structural formula

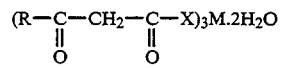

wherein R is a UV-absorbing aromatic group, X is an electron attracting group and M is a suitable metal ion, a suitable water-soluble organic solvent and water, at a pH of 3 to 10.

21 Claims, 3 Drawing Sheets

ENHANCEMENT OF POLYCYANOACRYLATE-DEVELOPED FINGERPRINTS

BACKGROUND OF THE INVENTION

1. Field of the Invention

This invention relates to the detection of fingerprints and the like, and in particular to the enhancement of polycyanoacrylate-developed fingerprints on human skin and other surfaces.

The skin is covered with a constantly changing film of sweat as the glands continuously secrete fluid, therefore any substance that is deposited on the surface of the skin is likely to be diluted and become blurred.

The sweat layer is a mixture of secretions from mainly eccrine and sebaceous glands (eccrine secretions; amino acids, urea, chlorides, and sugars; sebaceous secretions; fatty acids, glycerides, assorted hydrocarbons). Only eccrine glands are located on the palmar regions, and materials secreted from the sebaceous glands are transferred to the hands by touching areas such as the face and the back. (Detection of Fingerprints on Skin, D. S. Allman and C. A. Pounds, For. Sci. Rev. 3(2) 1991) Therefore it is possible that the materials deposited in a latent print may differ qualitatively and quantitatively from those of the skin surface on which the print is deposited.

After death the glands no longer secrete material and thus the dilution process ceases. The surface temperature will fall from that of live skin (near 32° C.) to ambient over a few hours. During this time the waxes and oils of the print will not be able to maintain their liquid state. However, before ambient temperature is reached diffusion may still occur on the postmortem surface leading to deterioration of ridge detail. Due to the absence of good detection methods for latents on skin this problem has not been well studied.

2. Description of the Prior Art

A number of techniques for the detection of fingerprints have been documented.

Fingerprints developed by cyanoacrylate ester (Super Glue) fumes on surfaces such as metals and plastic are well recorded in the literature. More specifically, the fingerprints develop a white residue on their ridges which is often visible to the naked eye as the cyanoacrylate ester molecules polymerize. This polymeric film provides a protective layer which helps preserve the ridge detail. The prints are easily seen on transparent surfaces. But on opaque surfaces (especially white ones) contrast may De poor. This makes it difficult to interpret print detail. Accordingly, dusting with powder or fluorescent dye staining is often used to enhance the print image.

There are many fluorescent dyes available for staining polycyanoacrylate ester such as Ardrox, Brilliant Yellow, Rhodamine-6-G and DCM. The dyes are applied as a methanol solution which is adsorbed onto the surface of the print as well as onto the background. Washing with fresh solvent to reduce the dye in the background also reduces the fluorescence intensity of the print. Fluorescence Is excited by a variety of high power light sources including the xenon arc lamp, Ar ion, Cu vapour or frequency-doubled Nd:YAG lasers. These are expensive high power light sources in the price range of $10-20,000 for lamps or over $100,000 for lasers. Such costly equipment restricts the availability of this technology to police forces which have large budgets.

A further disadvantage is the limitations of these techniques when applied to the detection of fingerprints on human skin. It cannot be overemphasized how important it would be to police authorities to have a technique suitable for the reliable detection of identifiable latent prints on murder victims.

Probably the most commonly used method for detecting prints on cadavers is the iodine-silver plate transfer technique, described for example in J. For. Sci. 22, 599 (1977) J. M. Adcock. The procedure involves fuming of the suspect area with iodine vapour which causes discoloration of the print. This is followed by the application of a polished silver plate to the print. Strong light is used to darken the silver iodide produced which can then be recorded by photography.

Powder techniques that have been applied to the recovery of prints on murder victims include the Magnabrush technique and the Kromekote® Lift technique. The methods rely on lifting of the print from the skin surface before the print can be identified. A significant level of print. detail will automatically be lost during the lifting process and this is one of the major disadvantages of such techniques.

Recently reports have appeared detailing the development of latent prints on human skin by cyanoacrylate fuming in a "tent" over the body followed by Rhodamine-6-G as a staining agent. However, the background fluorescence resulting from absorption of dye into the skin considerably reduces the contrast between the print and the background leading to loss of detail.

Further, in Fluorescent Metal-Ruhemann's Purple Coordination Compounds: Applications to Latent Fingerprint Detection, Journal of Forensic Sciences, JFSCA, Vol. 35, No. 1, Jan. 1990, pp. 25-34, E. R. Menzel et. al., latents were developed on paper with ninhydrin which reacts with the amino acids to give the dye Ruhemann's purple. This dye was then used to chelate europium ions thus becoming weakly fluorescent under laser illumination. The efficiency of this method is very low, and expensive time-resolved imaging is required to minimize the background fluorescence.

SUMMARY OF THE INVENTION

According to one aspect of the invention, a composition for enhancing the contrast of polycyanoacrylate-developed fingerprints and the like is provided, comprising a metal chelate of the structural formula I,

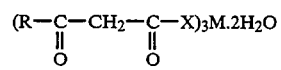

wherein R is an aromatic group capable of absorbing UV light,

X is an electron attracting group, and,

M is a suitable metal ion which upon exposure to sufficient UV radiation, intramolecularly receives UV energy absorbed by the chelate and emits the energy as visible fluorescence in a narrow wavelength emission band characteristic of the metal, a suitable water-soluble organic solvent, and water; at a pH of 3 to 10.

According to another aspect of the invention, a method for enhancing the contrast of polycyanoacrylate-developed fingerprints and the like is also provided, comprising (a) treating polycyanoacrylate-developed fingerprints with a composition comprising a metal chelate of structural formula I,

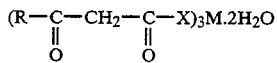

wherein R is an aromatic group capable of absorbing UV light,

X is an electron attracting group, and

M is a suitable metal ion which upon exposure to sufficient UV radiation, intramolecularly receives UV energy absorbed by the chelate and emits the energy as visible fluorescence in a narrow wavelength emission band characteristic of the metal, a suitable water-soluble organic solvent, and water; and wherein the pH of said composition is 3 to 10, to form a two-phase solution of (i) the solvent and water including dissolved chelate, and (ii) the solvent, excluding water but including dissolved chelate, in the cyanoacrylate polymer, wherein the dissolved chelate is transferred into the polycyanoacrylate through the organic solvent, (b) evaporating the solvent, leaving the chelate trapped in the polycyanoacrylate, and (c) illuminating with a suitable UV light source to excite the chelate.

DETAILED DESCRIPTION OF THE PREFERRED EMBODIMENTS

Figure 1:
FIG. 1 is a photograph of cyanoacrylate-developed fingerprints on a white polyethylene plastic bag, enhanced by a composition according to the invention.

Before the composition according to the invention is employed, the fingerprints are developed by the conventional cyanoacrylate process, as described for example in the Menzel et. al. Journal of Forensic Sciences article referenced above. In general, in this process alkyl-2-cyanoacrylates, typically ethyl-2-cyanoacrylate, is vapourized by heat to selectively polymerize on the ridges of the prints.

In the metal chelates of structural formula I,

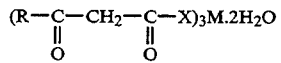

the R group is an aromatic UV-absorbing group including phenyl, substituted phenyl e.g. halo-substituted phenyl (such as fluorobenzene), heterocyclic aromatics (such as thiophene) and polycyclic aromatics (such as naphthyl). It will be appreciated that variations in the ring substituent will only shift the excitation wavelengths of the ligand, and provided that this wavelength remains in the UV region, the chelate will fluoresce in the red. Thiophene is preferred.

X is an electron attracting group. Specifically, an electron attracting group or atom is electronegative relative to its neighbouring atoms, and will withdraw electrons away from the neighbouring groups. Suitable groups include a $CY_3$ group, wherein Y is halogen including F, Cl, Br, I or At, and a halo-benzene group such as fluoro-benzene. $CF_3$ is preferred.

M is a suitable lanthanide metal ion, such as Tb and Eu which provides a narrow emission band (half height of about 10 nm). In the case of Eu III which is preferred, this band is centered at about 614 nm, thus giving an exceptionally large Stokes shift of about 260 nm.

For example, the chelate in which R is thiophene, X is $CF_3$ and M is europium III (i.e. the tris chelate of thenoyl trifluoroacetone and the europium III ion), may be purchased directly from Kodak. Alternatively, it may be synthesized as part of the enhancement process.

Specifically, the formation of an europium chelate involves an organic compound of the structural formula

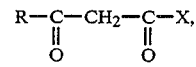

wherein R and X are as defined above.

The chelate forms in an aqueous buffered solution of pH 3 to 10 preferably about 8, containing $Du^{3+}$ ions, typically from a suitable Europium salt e.g. $EuCl_3.6H_2O$, which forms a single phase with the water-soluble organic solvent, containing the chelating ligand. Other europium salts may be used, such as the nitrate hydrate. Tris-amine buffer is preferred because it has no carbonyl groups which could preferably react with the metal ion.

Suitable organic solvents require the following properties:

partially water-soluble (20% or better), solubilizes metal chelate, penetrates, but does not dissolve the cyanoacrylate polymer, while retaining metal chelate in the polymer, and volatile (to evaporate readily, following penetration of polymer).

Suitable solvents include low molecular weight polar organic solvents incorporating a polar functional group, selected from a carbonyl group, a hydroxyl group and an ester group, such as ketones, alcohols and esters. Specific suitable solvents include lower-alkyl ketones (such as methylethyl ketone and diethyl ketone), ethyl acetate and 10% propanol or butanol, in water.

Lower-alkyl ketones are preferred as they contain a carbonyl group capable of displacing the two molecules of water surrounding the europium ion and binding to it, thereby creating (together with the ligand) a non-polar shell around the ion. The net effect is to increase the quantum yield. Methylethyl ketone is most preferred.

This composition is suitable for enhancing polycyanoacrylate developed fingerprints on many varied surfaces including plastics, metals, glass and human skin as will be apparent hereinafter.

When the polycyanoacrylate-developed fingerprints are treated with the composition according to the invention, the organic solvent replaces the water molecules bound within the europium chelate. The organic solvent also penetrates the polymeric cyanoacrylate without dissolving it and the chelate is transferred into the polymer. Thus, a two phase system is established i.e. (i) solvent in water including dissolved chelate and (ii) solvent excluding water, but including dissolved chelate in polycyanoacrylate. Thus, the europium chelate transfers into the solvent present within the polymer with a high partition ratio e.g. 100 to 1000 fold. The solvent is then removed by evaporation in air at room temperature. In other words, after removal from solution and evaporation of the solvent, the chelate remains trapped in the polycyanoacrylate in greatly increased concentration over that in solution.

The europium chelate is retained within the polymer and cannot be removed other than by dissolving the polymeric cyanoacrylate in a suitable polar solvent, such as acetone or dimethylsulfoxide.

Preferably, to further enhance the contrast, background fluorescence is minimized prior to UV illumination, by washing with a suitable organic solvent such as methanol, e.g. 70% methanol in water, to remove extraneous chelate adhering to the background material. Most preferably, the methanol wash includes 2–10% of a suitable non-ionic surfactant such as Tergitol ®, sold by Union Carbide under trade designation 15-S-7.

By these methods increased amount of chelate are transferred into the polycyanoacrylate print so that excitation by a cheap relatively low powered UV light source gives sufficient fluorescence to be easily seen by the eye.

EXPERIMENTAL

Formulation of europium chelate

Method of preparation of one litre working solution 1) 0.002M solution of Tris (Hydroxymethyl) aminomethane (tris amine buffer) is prepared and the pH is adjusted to 8 by addition of a suitable mineral acid, such as concentrated hydrochloric acid.

2) 455 mg of europium (III) chloride hexahydrate is dissolved in 780 ml of the buffered solution.

3) 1 g of thenoyltrifluoroacetone is dissolved into 220 ml. of methylethyl ketone.

4) The aqueous buffered europium-containing solution is added to the methylethyl ketone solution and shaken vigorously to mix.

In cases where there is a need to maintain the solution for long periods of time, mixing by ultrasound, resulting in a milky suspension, is recommended.

A solubilizer could be added to maintain the suspension for enhanced shelf-life. The basic criterion for the solubilizer is that the solubility of the dye in solution is improved, without detriment to the transfer of the chelate into the polymer.

It will be appreciated the thenoyltrifluoroacetone is provided in slight excess of the stochiometric amount required to form the chelate.

Detection of fingerprints on objects

Most common surfaces where fingerprints are found in criminal investigations are metal surfaces such as knives and handguns as well as plastic surface such as polyethylene bags used for trafficking drugs.

After treatment with cyanoacrylate ester in a conventional manner as described above, objects such as plastic bags are submerged for up to five minutes in a 10 times diluted working solution (MEK concentration 22%) contained in a bucket with a resealable lid to reduce the evaporation of methylethyl ketone.

Occasionally when transfer of the dye into polycyanoacrylate is weak, re-dipping for longer periods has proved successful.

On other surfaces such as metals, glass or hard plastics a fresh working solution is gently streamed onto the surface from a squeeze bottle.

On all surfaces after allowing the methylethyl ketone to evaporate, the surfaces are washed with alcohols (e.g. methanol) or other organic solvents which do not dissolve the polymer or remove the dye from the polymer, to reduce and often completely remove the background fluorescence which is caused by extraneous dye adhering to the background surface.

Figure 2:
FIG. 2 is a photograph of fingerprints on a revolver, enhanced by a composition according to the invention.
Figure 3:
FIG. 3 is a photograph of fingerprints on a galvanized metal surface, enhanced by a composition according to the invention.

FIGS. 1–3 show fluorescent prints on various surfaces photographed under UV light. A suitable light source is a 150 W mercury arc lamp that is completely blocked in the visible allowing only the 365 nm Hg line to pass the filter. Such lamps which produce an intensity of about 7 mw/cm$^2$ at 15" distance are available from several commercial sources at a cost of a few hundred dollars.

The fluorescent fingerprint is viewed through goggles that block the ultraviolet light. When using europium chelate, any background fluorescence from the substrate that is also excited by UV light may be greatly reduced by use of a narrow band (10 nm) interference filter centered at 620 nm and tilted slightly to pass a 614 nm central band.

DETECTION OF FINGERPRINTS ON SKIN

CA fuming of cadavers

The cadaver is enclosed within a frame which is covered by clear polyethylene. A heater for vapourizing cyanoacrylate is also present. As a control fingerprints are put down on aluminum foil and laid on the surface of the skin to obtain a similar temperature. The cadaver is sealed within the bag and exposed to the fumes for a minimum of one hour. It is advantageous to keep the humidity as low as possible.

Staining of poly-CA prints on skin

The areas where prints have developed and the cyanoacrylate polymer is visible to the eye are photographed by reflectance.

There are two techniques by which the freshly made print enhancing composition can be applied to these areas where prints were deposited.

Figure 4:
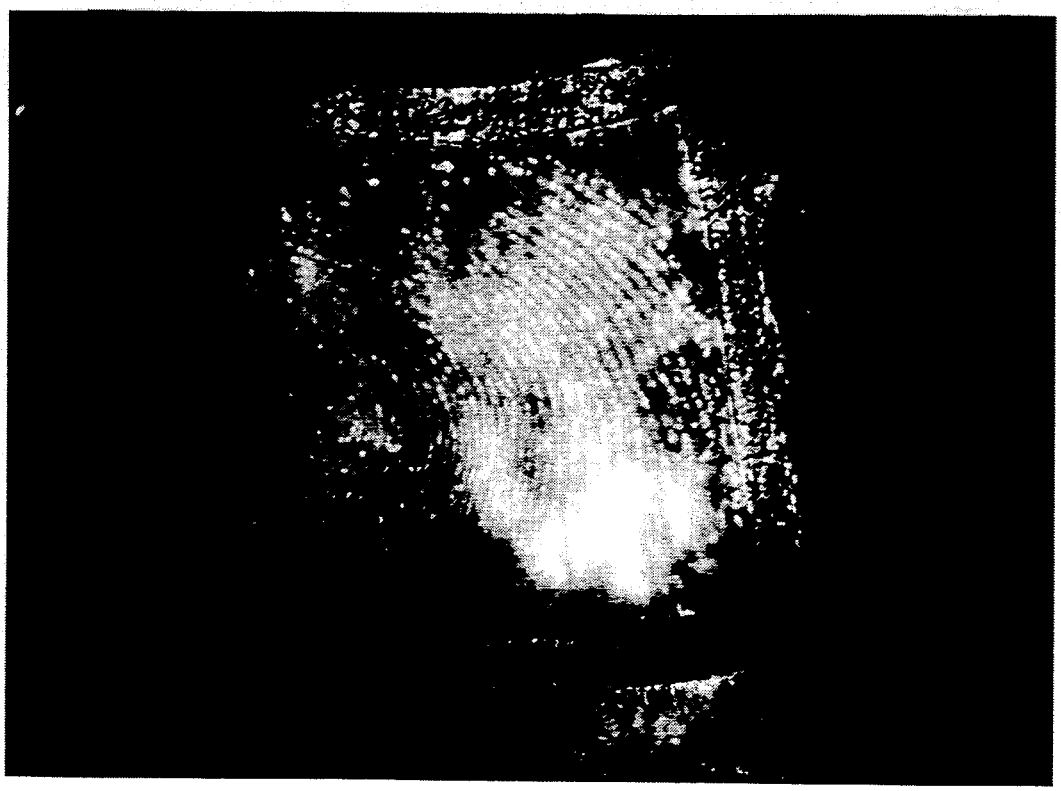
FIG. 4 is a photograph of polycyanoacrylate-developed fingerprints on a human cadaver, enhanced by a composition according to the invention.

One method requires strips of cotton wool to be gently laid on the surface. Specifically, a freshly made printenhancing composition of the invention is sprayed onto the cotton wool until this is thoroughly saturated. Then the cotton wool is pressed onto the skin and the region is wrapped in saran wrap to prevent excessive evaporation of methylethyl ketone. After 10 minutes, the saran wrap and cotton wool are removed and when viewed under UV light (a 150 W Mercury arc lamp as described above was employed) the region is fluorescent red. Gentle and repeated washing with methanol removes most the background fluorescence, revealing the dyed poly-cyanoacrylate print. (See FIG. 4).

Alternatively, after exposure to the cyanoacrylate a gentle stream of a freshly made print-enhancing composition according to the invention is allowed to flow over the cadaver by pressure from a squeeze bottle. This procedure which is now preferred, is performed under ultraviolet illumination. (A 150 W arc lamp as described above was employed.) The areas exposed to the solution will fluoresce red but as a rule the prints will be indistinct if visible at all. The skin is then rinsed in the same way with a ten percent solution of the non-ionic surfactant Tergitol ® (Union Carbide 15-S-7) in 70% methanol-water. The dye on the skin can be observed to flow away revealing the bright fingerprints which retain the dye. Occasionally for more persistent background fluorescence, cotton wool saturated with the wash solution can be laid on the surface of the skin until only the fingerprint fluorescence is visible.

Figure 5:
FIGS. 5 and 6 are photographs of prints on a human cadaver, before and after washing to reduce background fluorescence.
Figure 6:
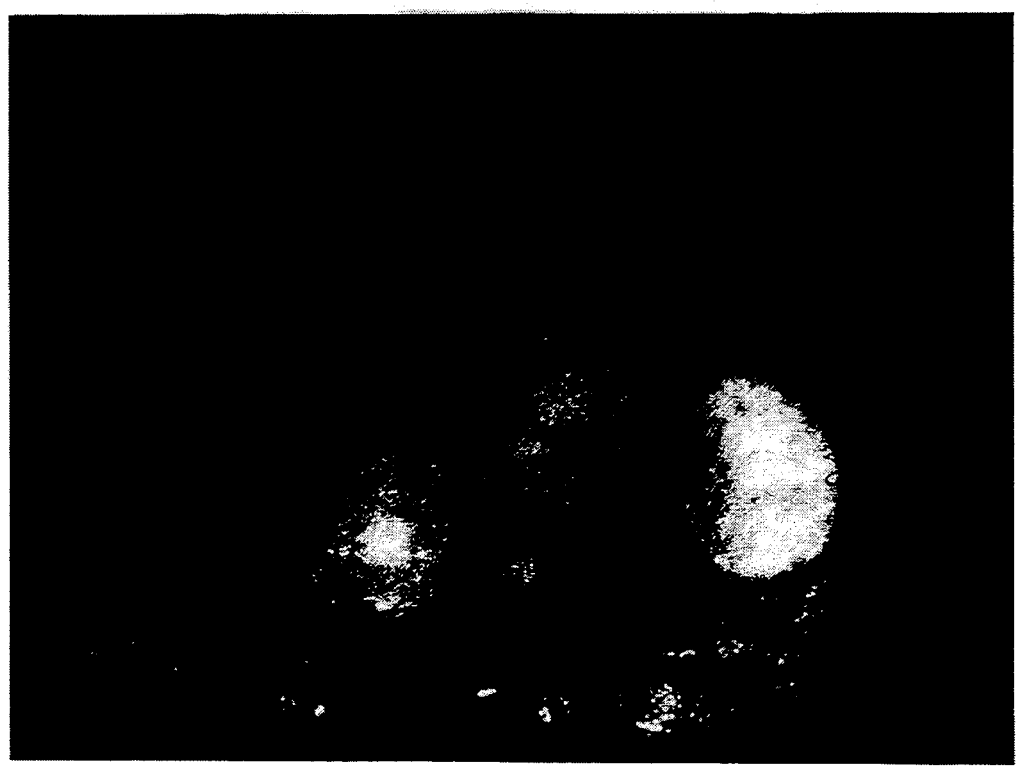

FIGS. 5 and 6 illustrate the same fingerprints on a human cadaver under UV illumination, before and after two washes with this wash solution.

Similar working solutions were made up as follows in the same manner using the same materials and amounts as described above, except that in step 3) in the organic compound the R and X groups are varied. Also, the europium salt is simply dissolved in water, rather than in the aqueous buffer.

Specifically, a second working solution was made up wherein R is phenyl and X is $CF_3$.

In a third working solution, R is naphthyl and X is $CF_3$.

In a fourth working solution, both R and X are fluorophenyl.

The same procedure as described above was then followed for the Detection of fingerprints on human skin, using each of the similar working solutions, in turn.

The second working solution was observed to exhibit a bright intense fluorescence. Print transfer was poor.

The third working solution produces a cloudy solution which appeared pale blue under UV. Print transfer was reasonable.

The fourth working solution also produced a cloudy solution which appeared bright red under UV. Print transfer was reasonable.

Accordingly, the thenoyltrifluoroacetone is preferred.

We the studied the effects of varying the organic solvent in step 3), using thenoyltrifluoroacetone. Again, the europium salt is dissolved in water, with no buffer or acid included. Specifically, the following solvents were employed 10% propanol, 10% butanol, 10% ethyl acetate, 5% ethyl acetate and 5% diethyl ketone.

For both alcohols and 10% ethyl acetate, very intense solution fluorescence occurred. However, transfer of dye into prints was poor and the background appeared blotchy.

For both 5% ethyl acetate and 5% diethyl ketone, very intense solution fluorescence also occurred. In both cases, very good print transfer was observed, but the background was blotchy.

Accordingly, methylethyl ketone is preferred.

For field use, the polycyanoacrylate fingerprint enhancing composition according to the invention may be provided in the form of a kit.

Specifically, the kit comprises a combination of two components which are maintained apart until use by kit means. The kit means includes separate containers for the two components and associated packaging. A plastic bag or enclosure could also be included to enclose the surface of interest.

More specifically, a first component comprises an organic compound of the structural formula

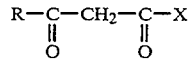

wherein R and X are as defined above, and the second component comprises a suitable salt of a metal ion, such as europium III chloride hexahydrate which after reaction with the first component to form a chelate, intramolecularly receives UV energy absorbed by the chelate and emits the energy as visible fluorescence in a narrow wavelength emission band characteristic of the metal, dissolved in an aqueous solution including a suitable buffer e.g. tris amine buffer, adjusted to about pH 8 by a suitable mineral acid, such as concentrated HCl. The first component may be dissolved in a suitable organic solvent as described above, such as methylethyl ketone. It will also be appreciated that the second component is most conveniently provided in solution, in view of the transport regulations for concentrated HCl.

For example, for a one litre working solution, a first reactant includes a concentrate of 1 g of thenoyltrifluoroacetone dissolved in 22 ml of methylethyl ketone. The second reactant includes a concentrate of 455 mg of europium III chloride hexahydrate dissolved in 78 ml of an aqueous solution adjusted to pH 8 by HCl, and tris amine buffer pH 8. At the time of use, a working solution would be completed by the addition of sufficient additional amounts of water and methylethyl ketone. Vigorous mixing provides a working solution with a concentration of about 22% methylethyl ketone in 1 l of solution. Such a solution would be useful for use with human cadaver skin and metal objects. It will be appreciated that various kits may be sold in which the amounts of the reactants in the two components are scaled up to provide different amounts of working solution. For example, a 10 l working solution would be provided by 10 g of thenoyltrifluoroacetone and 4.55 g of europium III chloride hexahydrate.

A less concentrated solution would be used for other background substrates. For example, on plastic objects, a 0.1 g of the thenoyl compound and 45 mg of europium salt could be used, per litre of solution.

We claim:

1. A method of enhancing the contrast of polycyanoacrylate-developed fingerprints, comprising
   (a) treating polycyanoacrylate-developed fingerprints with a composition comprising metal chelate of structural formula I,

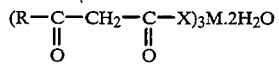

wherein R is an aromatic group capable of absorbing UV light, X is an electron attracting group, and M is a suitable metal ion which upon exposure to sufficient UV radiation, intramolecularly receives UV energy absorbed by the chelate and emits the energy as visible fluorescence in a narrow wavelength emission band characteristic of the metal, a suitable water soluble organic solvent, and water; and wherein the pH of the composition is 3 to 10, to form a two-phase solution of (i) the solvent and water including dissolved chelate and (ii) the solvent, excluding water but including dissolved chelate, in the cyanoacrylate polymer, (b) evaporating the solvent leaving the chelate trapped in the cyanoacrylate polymer, and (c) illuminating with a suitable UV light source to excite the chelate.

2. A method according to claim 1, wherein the organic solvent includes a polar functional group selected from a carbonyl group, a hydroxyl group and an ester group.

3. A method according to claim 2, wherein the organic solvent is a lower-alkyl ketone.

4. A method according to claim 3, wherein the organic solvent is methylethyl ketone.

5. A method according to claim 4, wherein the composition additionally comprises a suitable buffer, and wherein the pH is adjusted to about 8, by means of a suitable mineral acid.

6. A method according to claim 5, wherein the buffer is Tris amine buffer, pH 8.

7. A method according to claim 6, including the additional step of washing the fingerprints with a washing solution of 2–10% of a suitable non-ionic surfactant in methanol.

8. A method according to claim 7, wherein the dissolved chelate is transferred into the polycyanoacrylate in a partition ratio of 100 to 1000 fold.

9. A method according to claim 7, wherein prior to step (a) the composition is sonicated by ultrasound.

10. A method according claim 7, wherein the metal chelate is the tris chelate of thenoyltrifluoroacetone and the europium III ion.

11. A method according to claim 1, wherein the fingerprints are on human cadaver skin.

12. A kit for enhancing the contrast of polycyanoacrylate-developed fingerprints, comprising in combination (a) an organic compound of the structural formula

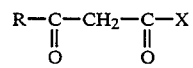

wherein R is an aromatic UV absorbing group and X is an electron attracting group, (b) a suitable europium III salt, dissolved in an aqueous solution adjusted to a pH of about 8 by a suitable mineral acid and a suitable buffer pH 8, and (c) kit means to separately contain and maintain apart until use, predetermined amounts of (a) (b).

13. A combination according to claim 12, wherein at the time of use (a) and (b) are combined and mixed vigorously with additional water and organic solvent to provide a working solution including about 22% of organic solvent.

14. A combination according to claim 3, wherein (a) the organic compound is dissolved in a suitable organic solvent.

15. A combination according to claim 14, wherein the organic solvent is methylethyl ketone.

16. A combination according to claim 15, wherein the buffer is tris amine buffer pH 8.

17. A combination according to claim 16, wherein the salt is europium III chloride hexahydrate.

18. A combination according to claim 17, wherein the organic compound R is thiophene and X is $CY_3$, where Y is halogen including astatine.

19. A combination according to claim 18, wherein X is $CF_3$.

20. A combination according to claim 13, wherein (a) includes 0.1 to 1 g of thenoyltrifluoroacetone, and wherein (b) includes 45 to 455 mg of europium III chloride hexahydrate, per litre of solution.

21. A combination according to claim 13, wherein (a) includes about 10 g of thenoyltrifluoroacetone, and wherein (b) includes about 4.55 g of europium III chloride hexahydrate dissolved in about 78 ml of the aqueous solution.

* * * * *